United States Patent [19]
den Dulk

[11] Patent Number: 5,374,280
[45] Date of Patent: Dec. 20, 1994

[54] DUAL CHAMBER PACEMAKER SYSTEM AND METHOD FOR DELIVERING ATRIAL SYNC PULSES

[75] Inventor: Karel den Dulk, WV Maastricht, Netherlands

[73] Assignee: Medtronic, Inc., Minneapolis, Minn.

[21] Appl. No.: 178,349

[22] Filed: Jan. 6, 1994

Related U.S. Application Data

[63] Continuation of Ser. No. 830,089, Feb. 3, 1992, abandoned.

[51] Int. Cl.⁵ .................................................. A61N 1/368
[52] U.S. Cl. .......................................................... 607/14
[58] Field of Search ........................................ 607/9, 14

[56] References Cited

U.S. PATENT DOCUMENTS

| | | | |
|---|---|---|---|
| 4,593,695 | 6/1986 | Wttikampf | 128/419 PG |
| 4,686,989 | 8/1987 | Smyth et al. | 128/419 PG |
| 4,714,079 | 12/1987 | Hedberg et al. | 607/14 |
| 4,781,194 | 11/1988 | Elmquist | 607/14 |
| 4,788,980 | 12/1988 | Mann et al. | 128/419 PG |
| 4,856,521 | 8/1989 | Irnich | 128/419 PG |
| 4,856,524 | 8/1989 | Baker, Jr. | 128/419 PG |
| 4,890,617 | 1/1990 | Markowitz | 128/419 PG |
| 4,905,696 | 3/1990 | Amundson et al. | 128/419 PG |
| 4,920,965 | 5/1990 | Funke | 128/419 PG |
| 4,951,667 | 8/1980 | Markowitz | 607/9 |
| 5,027,815 | 7/1991 | Funke | 607/9 |
| 5,123,412 | 6/1992 | Betzold | 128/419 PG |
| 5,129,393 | 7/1992 | Bromwell | 128/419 PG |
| 5,144,950 | 9/1992 | Stoop et al. | 128/419 PG |
| 5,273,035 | 12/1993 | Markowitz et al. | 607/14 |

FOREIGN PATENT DOCUMENTS

2141347 12/1984 United Kingdom ......... 128/419 PG

*Primary Examiner*—William E. Kamm
*Attorney, Agent, or Firm*—Reed A. Duthler; Harold R. Patton

[57] ABSTRACT

A dual chamber pacemaker is provided, preferably either DDDR or DDIR, having logic hardware and/or software for normally carrying out the DDIR or DDDR mode of operation, and further having means for avoiding delivery of an atrial pace pulse in circumstances where normal atrial pacing could otherwise be competitive or result in loss of atrial capture. The pacemaker has means for detecting an atrial sense during PVARP, timing out a delay from the time of the early atrial sense, and inhibiting delivery of an atrial pulse during the delay. In a preferred embodiment, the ventricular rate, which may be established by a rate responsive sensor, is maintained, while atrial sync pulses are delivered whenever possible following an early atrial sense so as to provide synchronous pacing whenever that is consistent with safe atrial pacing and substantial regularity of the ventricular pacing.

14 Claims, 5 Drawing Sheets

DDI R + ASP, PVARP=VAei

FIG. 6B

DUAL CHAMBER PACEMAKER SYSTEM AND METHOD FOR DELIVERING ATRIAL SYNC PULSES

This is a continuation of copending application Ser. No. 07/830,089 filed on Feb. 3, 1992, now abandoned.

CROSS REFERENCE TO CO-PENDING APPLICATION

Reference is made to U.S. patent application Ser. No. 07/829,811, by Markowitz, filed as of the date of the present application.

BACKGROUND OF THE INVENTION

1. Field of the Invention

This invention relates to cardiac pacemakers and, more particularly, to dual chamber pacemakers and methods of pacing which optimize pacemaker response to early sensed atrial beats.

2. Description of the Prior Art

Various types of pacemakers are disclosed in the prior art, and are presently in widespread use. The pacing literature has documented the different types of pacemakers and their characteristics extensively. An excellent summary of the evolution and characteristics of pacemaker types, and specifically different types of dual chamber pacemakers, is set forth in U.S. Pat. No. 4,951,667, Markowitz et al., which is incorporated herein by reference.

Another and more recent advance in the field of cardiac pacing systems is that of the rate responsive pacemaker which increases cardiac output in response to exercise or other body demands. Such pacemakers may control pacing rate based upon sensing any one or a combination of different body parameters such as body activity, blood pH, respiratory rate, QT interval or historical atrial activity. See, for example, U.S. Pat. No. 4,428,378, Anderson et al., disclosing a pacemaker which varies pacing rate in response to sensed patient activity; and U.S. Pat. No. 4,228,308, Rickards, which discloses controlling pacing rate in response to Q-T interval. Additionally, rate responsive control has been integrated into dual chamber pacing systems, e.g., DDDR and DDIR systems. See "Rate Responsive Dual Chamber Pacing" in *PACE*, vol. 9, pp. 987–991; U.S. Pat. No. 4,467,807, Bornzin; and the above-noted U.S. Pat. No. 4,951,667.

A problem that has been recognized as arising in dual chamber pacemakers is that of "competitive atrial pacing" where, following an early natural atrial depolarization, the pacemaker may either fail to achieve atrial capture with a subsequent atrial pace pulse, or may induce an arrhythmia due to delivery of the atrial pacing pulse too closely following the atrial depolarization. Dual chamber pacing at rapid rates using prior art pacemakers may result in pacing the atrium near and possibly within the atrial cardiac refractory period of PACs and retrograde P waves. If atrial pacing occurs within the natural refractory period of the atrium, i.e., the refractory period of the heart, not that of the pacemaker, the pace stimulus will not capture the atrium. In such a situation, the actual interval between atrial and ventricular depolarizations may be prolonged beyond the physician-programmed AV interval. Further, if atrial stimuli are delivered such that they fall not in the natural refractory period of the atrium, but immediately afterwards, there exists the potential to initiate atrial fibrillation, atrial flutter, or other re-entrant tachycardias. This likelihood is especially prevalent in patients with a prior history of atrial arrhythmias.

One prior art response to the detection of a PAC is to switch the mode of the dual chamber pacemaker into a mode of operation not synchronized to the atrium, i.e., sacrifice atrial synchronous operation and deliver only ventricular pacing pulses until natural atrial signals are sensed having timing which enables switching back to atrial synchronous operation. See, for example, the patent to Funke et al., U.S. Pat. No. 5,027,815, also incorporated herein by reference, where the response to an early atrial sense is to simply inhibit delivery of an atrial pulse and proceed to deliver the ventricular pulse at the scheduled time. In this type of dual chamber system, ventricular rate regularity is maintained, but at the expense of AV synchrony.

Switching to a mode of operation in which ventricular pacing is not synchronized to the atrium or pacing the atrium at a time which causes loss of atrial capture with a resultant long AV interval, has the adverse effect of hemodynamic loss of the atrial kick on ventricular filling, and decrease in subsequent cardiac output. Also, a long interval between atrial and ventricular depolarizations allows the normal AV conduction system to repolarize and conduct retrogradely to the atrium. In this manner, the patient may suffer from the contraction of the atria on closed AV valves (i.e., the pacemaker syndrome) and even worse, the patient may be subject to initiation of pacemaker-mediated tachycardia (PMT). Maintaining short or reasonable AV intervals is critical to prevention of PMT.

A response to these concerns is found in the patent to Markowitz et al., U.S. Pat. No. 4,951,667, incorporated herein by reference. The pacemaker of this patent responds to an atrial sense (AS) that is deemed early by delaying the timing of the atrial pulse (AP) which is to be delivered. The scheduled VA interval is normally set by a sensor, i.e., it is a rate responsive interval. When and if a natural atrial signal is sensed within a relative atrial refractory period following a paced or sensed ventricular depolarization, and also within a safety period just preceding the time out of the scheduled VA escape interval, then the VA interval is shifted to a longer interval corresponding to a pre-set lower rate instead of the sensor determined V-A interval. Thus, instead of delivering an atrial pulse at the normal scheduled time, it is delayed following such an early atrial sense, and the ventricular pace pulse (VP) is synchronized to the delayed atrial pace pulse. The resulting beat to beat variability of the pacing rate may be substantial.

There thus remains a need for a pacemaker, and method of pacing which maintains safe, synchronized dual chamber pacing wherever possible and maintains a regular ventricular paced rhythm. It is undesirable from both hemodynamic and electrophysiologic rationales to allow atrial pacing during times at which the pacemaker may either fail to capture or may induce an arrhythmia. It is also undesirable to allow large beat-to-beat variations in ventricular paced rhythm. It is the intention of the atrial sync pace feature of this invention to reduce the occurrences of such behavior, and to deliver safe atrial pulses in a timed relation to subsequent ventricular pulses so as to maintain an appropriate ventricular pacing rate and to maintain AV synchrony whenever possible.

SUMMARY OF THE INVENTION

It is an object of this invention to provide a dual chamber pacemaker, and corresponding method of operation, which responds to an early atrial sense event so as to maintain AV synchronous operation where possible, while still avoiding atrial competition and maintaining ventricular rate regularity. In particular, it is an object of this invention to continuously monitor early atrial senses and respond to them appropriately.

The atrial sync pace feature of the present invention is particularly valuable in the context of a rate responsive, dual chamber pacemaker of the type in which the pacer's basic escape interval is varied as a function of a physiologic sensor (e.g. DDDR and DDIR pacers). In such devices, the interval between ventricular pacing or sensing and the subsequent scheduled delivery of an atrial pacing pulse may be quite short. Typically, in such devices a refractory period is defined following delivery of a ventricular pacing pulse or sensing of a ventricular depolarization. During this refractory period, a sensed atrial depolarization will not be effective to initiate timing of the AV interval. In prior art devices, atrial depolarizations which fall within this interval, typically referred to as the "post ventricular atrial refractory period" or "PVARP", were ignored, and a pacing pulse was delivered to the atrium at the expiration of the V-A interval. In most prior art DDD-type pacemakers, this functional arrangement did not pose significant problems, as the time differential between expirations of the PVARP and expiration of the V-A interval was sufficient to assure than an atrial pacing pulse would not be delivered in close proximity to an atrial depolarization occurring during the PVARP.

Therefore, it is in the context of a pacemaker which includes the possibility of varying the duration of its V-A intervals that the atrial sync pace pulse feature is most likely to be employed. In such devices, an atrial depolarization sensed in close proximity to a preceding ventricular depolarization presents a problem to the pacemaker. Simply synchronizing the delivery of a subsequent ventricular pulse to the sensed early atrial depolarization is often undesirable, as it may result in an excessive heart rate. Simply inhibiting the delivery of the subsequent scheduled atrial pacing pulse may result in a prolonged AV interval, leading to the possibility of retrograde conduction as discussed above. Delivering the scheduled atrial pacing pulse at the expiration of the V-A interval may result in competitive atrial pacing. Falling back to the base pacing rate as discussed in the above-cited Markowitz et al. patent preserves AV synchrony at the expense of preserving the sensor indicated pacing rate. The present invention simultaneously addresses all of these problems.

In view of the above objects, there is provided a dual chamber pacemaker, preferably a rate responsive pacemaker with a varying atrial escape interval. The pacemaker has means for establishing a post-ventricular atrial refractory interval (PVARP) and for identifying when an early atrial sense event occurs within such PVARP, and for inhibiting delivery of an atrial pulse for a time AIW (atrial inhibition window) following the occurrence of such an atrial sense event. If the AIW ends before the scheduled atrial escape interval, there is no change in operation, i.e., an atrial pace is delivered at the end of the atrial escape interval the (V-A interval) in the absence of an intervening sensed atrial or ventricular depolarization.

For cases in which the AIW ends after the atrial escape interval (V-A interval), the pacemaker further provides control means responsive to such an early atrial sense for delivering an atrial sync pulse (ASP) whenever such a pulse can be delivered at least a minimum AV interval ($AV_{min}$) before the time $t_{vv}$ of the normal scheduled ventricular pulse, and after the end of the AIW time period. When these conditions are met, the ASP is delivered at the calculated time of the end of AIW, and a synchronous ventricular pulse is delivered at $t_{vv}$.

If the above conditions cannot be met, the pacemaker may determine whether the ventricular escape interval (V-V interval) can be extended by a predetermined increment delta, so as to enable delivery of both an ASP at the end of the AIW, and a ventricular pacing pulse within the extended ventricular escape interval and at least an $AV_{min}$ delay from the ASP. If this cannot be done, then the atrial pulse is inhibited entirely and the ventricular pulse (VP) is delivered at $t_{vv}$, the scheduled end of the ventricular escape interval. As an alternative, an ASP may be delivered at the end of the AIW synchronous to or even following $T_{vv}$.

One result of the atrial sync pulse feature of the present invention is that in a DDDR pacer, in the presence of simultaneous high atrial rates and high sensor indicated pacing rates, the atrial sync pulse feature operates to effectively change the pacing mode of the device from DDDR to DDIR. This "mode switch" occurs only in those circumstances in which atrial synchronized ventricular pacing is not practical at or near the sensor indicated pacing rate. Thus, the atrial sync pulse invention also provides a simple alternative to more complicated mode switching algorithms that have been recently proposed to address the interaction of atrial and sensor indicated rates.

DESCRIPTION OF THE PREFERRED EMBODIMENTS

The following symbols are used in the specification to define events, intervals, and times:

| | |
|---|---|
| AS | atrial sense |
| ASR | atrial sense during PVARP |
| AP | atrial pace |
| ASP | atrial sync pulse |
| VP | ventricular pace |
| EI | escape interval; if not otherwise specified, it is $VA_{ei}$ |
| $VA_{ei}$ | interval from V event to delivery of a scheduled AP |
| $VV_{ei}$ | interval from V event to scheduled delivery of a VP |
| AIW | interval timed out after an early atrial sense, and representing period of vulnerability or inexcitability of the atrium |
| $t_w$ | time when AIW ends |
| $AV_{min}$ | the minimum AV interval during safe atrial pacing operation to which the AV interval may be compressed |
| $t_{ASP}$ | calculated latest time of ASP |
| $t_{VA}$ | time when $VA_{ei}$ ends |
| $t_{vv}$ | time when $VV_{ei}$ ends |
| $t_{AS}$ | time of early atrial sense |
| DDD? | DDD or DDDR mode |
| DDI? | DDI or DDIR mode |
| PVARP | post-ventricular atrial refractory period |
| PVAB | post-ventricular atrial blanking |
| PAV | paced AV interval, i.e., AV interval to follow atrial pacing |
| SAV | sensed atrial interval, i.e., AV interval to follow sensed atrial beat |

In the following discussion, the pacemaker is illustrated as being ventricular-time-based, i.e., timing is referenced to the ventricular event. It is to be noted that atrial, or A-A timing is equally suitable for this invention. Thus, for example, the atrial escape interval may be the V-A time, or the A-A time; the ventricular escape interval may be calculated as A-A minus AV interval, etc. However, V-V timing and terminology is used consistently to simplify illustration of the invention.

Figure 1:
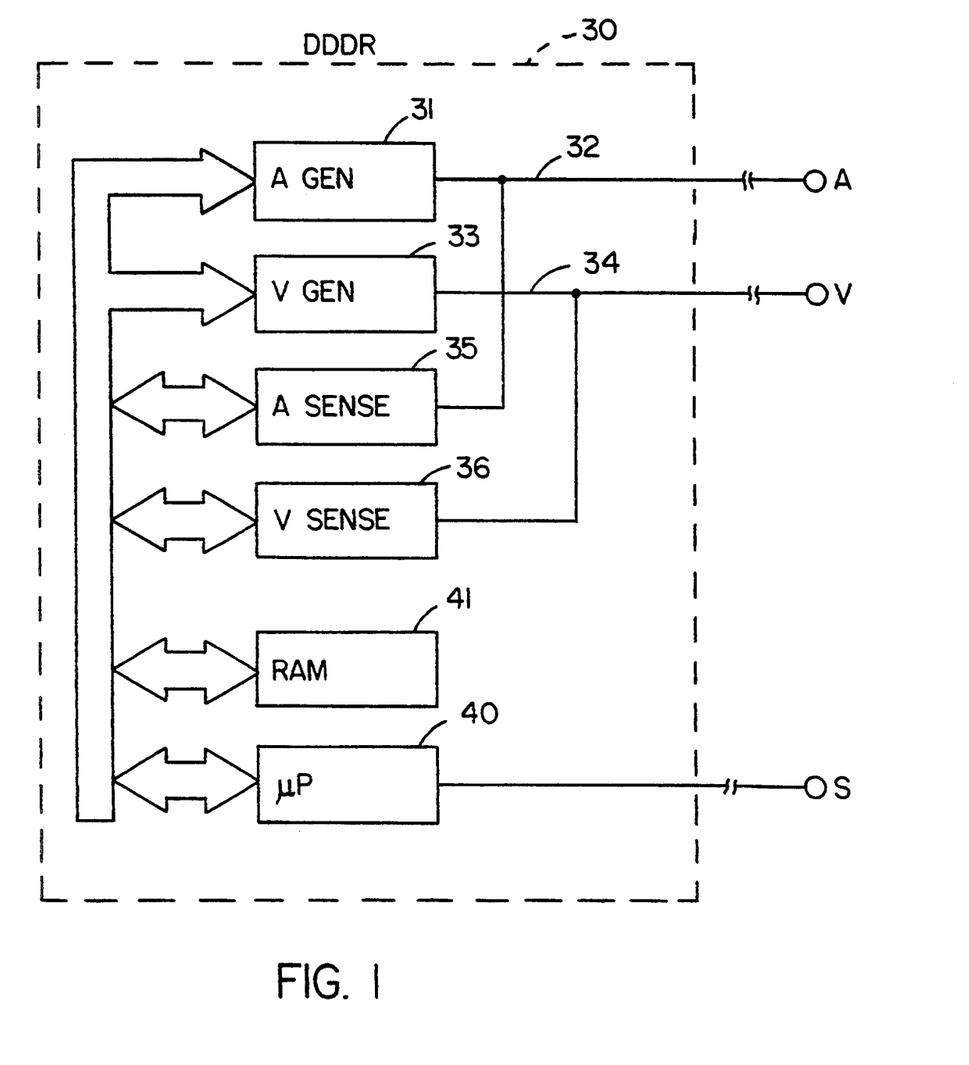
FIG. 1 is an illustrative block diagram of the components of the dual chamber pacemaker system as utilized by this invention, showing the relationship of the control unit to the primary signal sensing and stimulus generating elements.

Referring now to FIG. 1, there is shown a basic block diagram of the primary hardware components of a DDDR pacer 30, it being noted that the invention is also applicable to other types, e.g., DDI, DDIR and DDD. An atrial pacing pulse generator 31 is shown, which is connected to the patient's atrium through lead 32, for delivery of pacing pulses. An atrial sense amplifier 35 is illustrated, also connected to atrial lead 32, to receive and sense signals from the patient's atrium. A ventricular pacing pulse generator 33 is illustrated which is connected to the patient's ventricle through lead 34, to deliver pacing pulses, and a ventricular sense amplifier 36 is also connected to lead 34, to receive and sense signals from the patient's ventricle. Generators 31 and 33, and sense amplifiers 35 and 36, are interconnected with microprocessor 40, and/or other desired control hardware 41, for control of timing of pulse delivery, blanking, refractory intervals, and the like, in a well known matter.

Microprocessor 40 suitably has software stored in memory 41 to control the operation of the hardware units. Such software control is well known in the art, and has been incorporated into both external and implantable commercial pacemakers. As affects the scope of this invention, the degree to which software supplants hardware, or vice-versa, is a matter of design choice. Thus, for the timing functions that are carried out in the pacing system of this invention, it is to be understood that the microprocessor may have built-in timing circuits, or suitably may control external hardware timer circuits. Software control of pacing functions is well known in the art, such that the following detailed discussions of the timing and software specifications enable one of ordinary skill in this art area to design a system for carrying out the required functions within the scope of the invention.

A sensor S is illustrated as providing an input to the microprocessor 40. Sensor S is understood to be representative of any type of sensor, or combination of sensors, as known in the pacer art for developing one or more signals from which a desired sensor pacing rate can be developed. Although the sensor S is illustrated as being outside of the pacemaker 30, it can be positioned within or without the pacemaker housing. Likewise, a body parameter representative of desired pacing rate may be derived from one of the pacing leads, e.g., the QT pacemaker of the above-noted U.S. Pat. No. 4,228,803. A DDDR pacemaker also has hardware and/or software for transforming the sensed signal or signals into a desired sensor rate control signal, for controlling pacing rate, in a known fashion. Thus, in a rate responsive pacemaker of this invention, the atrial escape interval and/or ventricular escape interval may be varied as a function of rate signals, which rate signals are derived from one or more sensors and/or the natural atrial rate.

Figure 2:
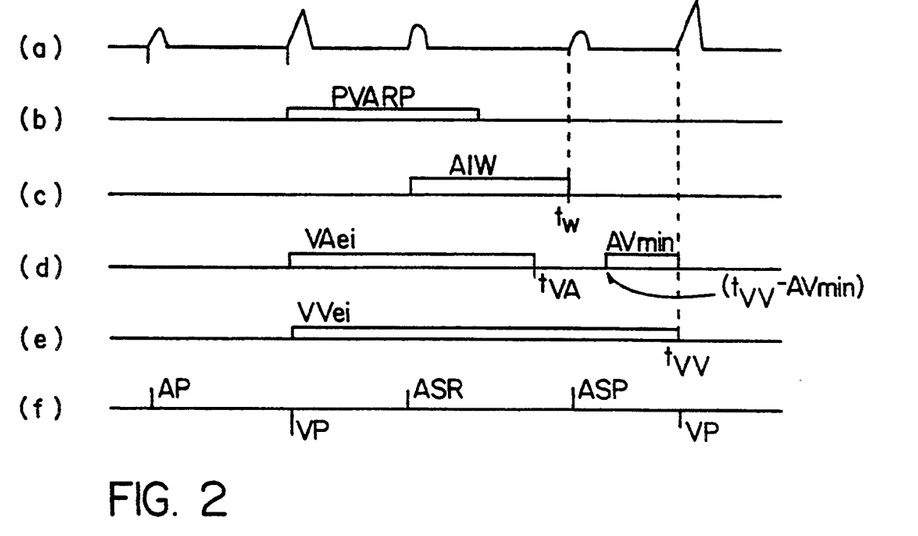
FIG. 2 comprises timing diagrams (a) through (f) illustrating the operative response of a pacemaker of this invention to early atrial senses which are identified as requiring an anti-competitive atrial response, and where an atrial sync pulse is delivered.

Referring now to FIG. 2, timing diagrams (a) through (f) illustrate the situation where an ASP is delivered following an ASR, followed by a synchronized ventricular pulse (VP), at the regularly scheduled ventricular rate; the ASP is timed to avoid competition while continuing to provide A-V synchrony.

As used in this specification, the term PVARP is the period of time during which a sensed atrial signal is not used to initiate an AV interval. As disclosed herein, the term "early atrial sense period" corresponds to the PVARP. In any case, the early atrial sense period includes a timed period following each ventricular event when an AS is not used to initiate an AV interval, whether the pacemaker initiates timing following atrial or ventricular events.

The present invention may be practiced in pacemakers which employ a pseudo-Wenckebach function, in which an atrial event which occurs following the PVARP will initiate an AV interval which expires at the later of a ventricular upper rate interval or the programmed duration for the AV interval. Similarly, the invention may also be practiced in pacers in which the sum of the PVARP and the programmed AV interval defines the upper tracking rate.

Still referring to FIG. 2, the EKG is illustrated in diagram (a), where a first atrial pace and ventricular pace are illustrated, followed by an ASR. Diagram (b) shows the effective PVARP in timed relation to the first VP, it being seen that an atrial sense (ASR) falls within PVARP. At this time, a delay period AIW is initiated, the termination of which is indicated as $t_w$, as seen in diagram (c). Diagram (d) illustrates the atrial escape interval ($VA_{ei}$), as well as the $AV_{min}$ interval and the calculation of $t_{asp} = t_{vv} - AV_{min}$. Diagram (e) shows the ventricular escape interval ($VV_{ei}$), which ends at $t_{vv}$. The calculated $t_{asp}$, $t_{vv} - AV_{min}$, occurs after the end of the AIW delay ($t_w$). Thus, the atrial pacing pulse is delivered at $t_w$. Diagram (f) is a marker channel representation of the cycle. It is to be noted that in this case the AV delay has been compressed, but is longer than $AV_{min}$. The result of this arrangement is that following the ASR, an ASP is delivered at $t_w$, a safe interval following the early atrial sense (ASR), maintaining AV synchrony and regularity of the ventricular rate.

Figure 3:
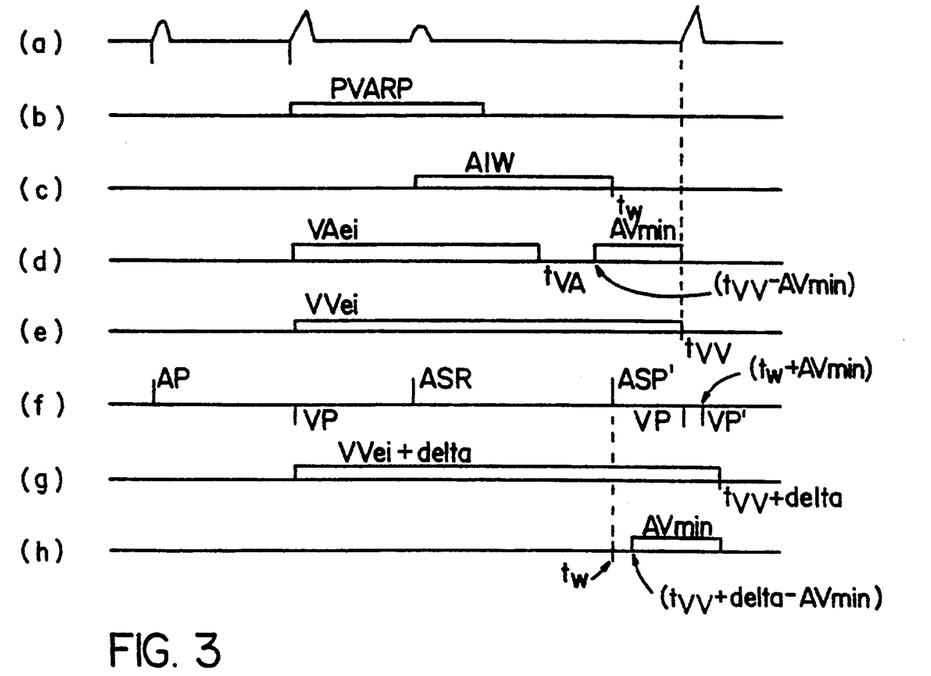
FIG. 3 comprises timing diagrams (a) through (f) illustrating the operative response of a pacemaker of this invention to early atrial senses which are identified as requiring an anti-competitive atrial response, and wherein the timing is such that either no atrial sync pulse is delivered or the ventricular pulse is delayed to accommodate an atrial sync pulse.

Referring to FIG. 3, diagrams corresponding to FIG. 2 are shown, but $VA_{ei}$ and $VV_{ei}$ are somewhat shorter, e.g., due to sensor or rate responsive control. In this situation, it is seen that even with a minimum AV delay, the calculated latest time ($t_{ASP}=t_{vv}-AV_{min}$) for delivering an ASP comes too early, i.e., before the end of the AIW interval ($t_w$). For this reason, no ASP is delivered, but a ventricular stimulus VP is delivered at $t_{vv}$.

Thus, in reviewing FIGS. 2 and 3, together, it is seen that in a first embodiment of the pacemaker of this invention, in response to an early atrial sense: (a) ventricular rate is maintained; and (b) the pacemaker maintains synchronous operation whenever possible, by delivering an ASP at the end of the AIW so long as the VP at $t_{vv}$ follows by at least $AV_{min}$. In practice, a typical value for AIW is 300 ms, and for $AV_{min}$ it is 40 ms; both of these values can be selected by the physician who can program them into the pacemaker in a well known manner.

An alternative embodiment is also illustrated in FIG. 3, in diagrams f, g and h. As illustrated, if $t_{ASP}(t_{vv}-AV_{min})$ comes too early (before $t_w$), the pacer may optionally add a predetermined increment delta to the ventricular escape interval and check to determine whether extending the ventricular escape interval to $t_{vv}+$ delta will allow for delivery of an atrial sync pulse. If $t_{vv}+$ delta$-AV_{min}$ is not before $t_w$, an atrial sync pulse ASP' is delivered at $t_w$ and a ventricular pacing pulse VP' is delivered at $t_w+AV_{min}$, in the absence of intervening ventricular depolarizations.

Figure 4:
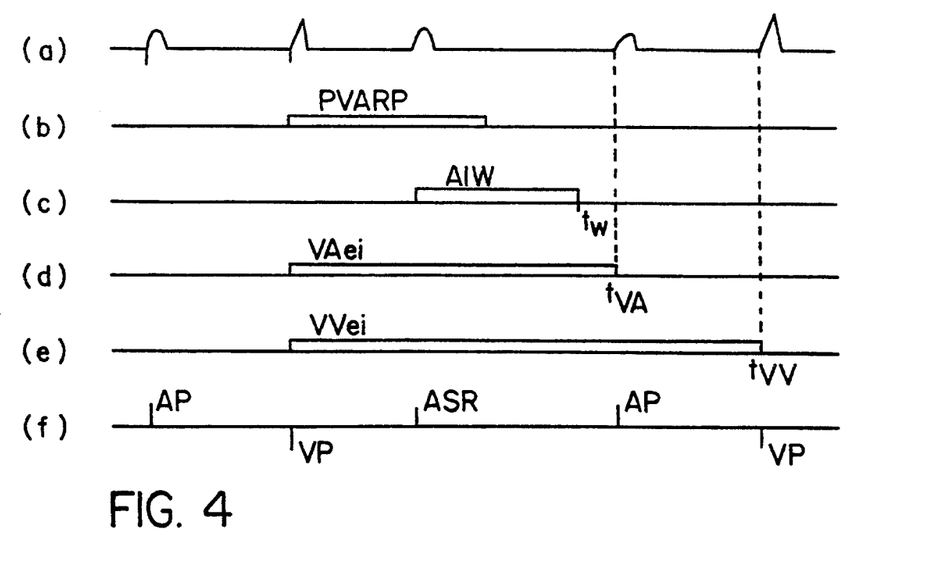
FIG. 4 comprises timing diagrams illustrating atrial and ventricular events and pacemaker time periods, for an illustrative situation where an early atrial sense does not alter the scheduled delivery of atrial and ventricular paces.

FIG. 4 illustrates a situation where $VA_{ei}$ is longer than for FIG. 3, such as where the sensor calls for a lower pacing rate. Here, $t_w$ is calculated to occur before the end of $VA_{ei}$ ($t_{VA}$). In such a situation, the normally scheduled escape intervals can be maintained, so that there is no ASP delivered and the AP is delivered at scheduled $t_{VA}$. Thus, the early atrial sense does not alter the normal DDDR or DDIR operation in such situations.

Figure 5:
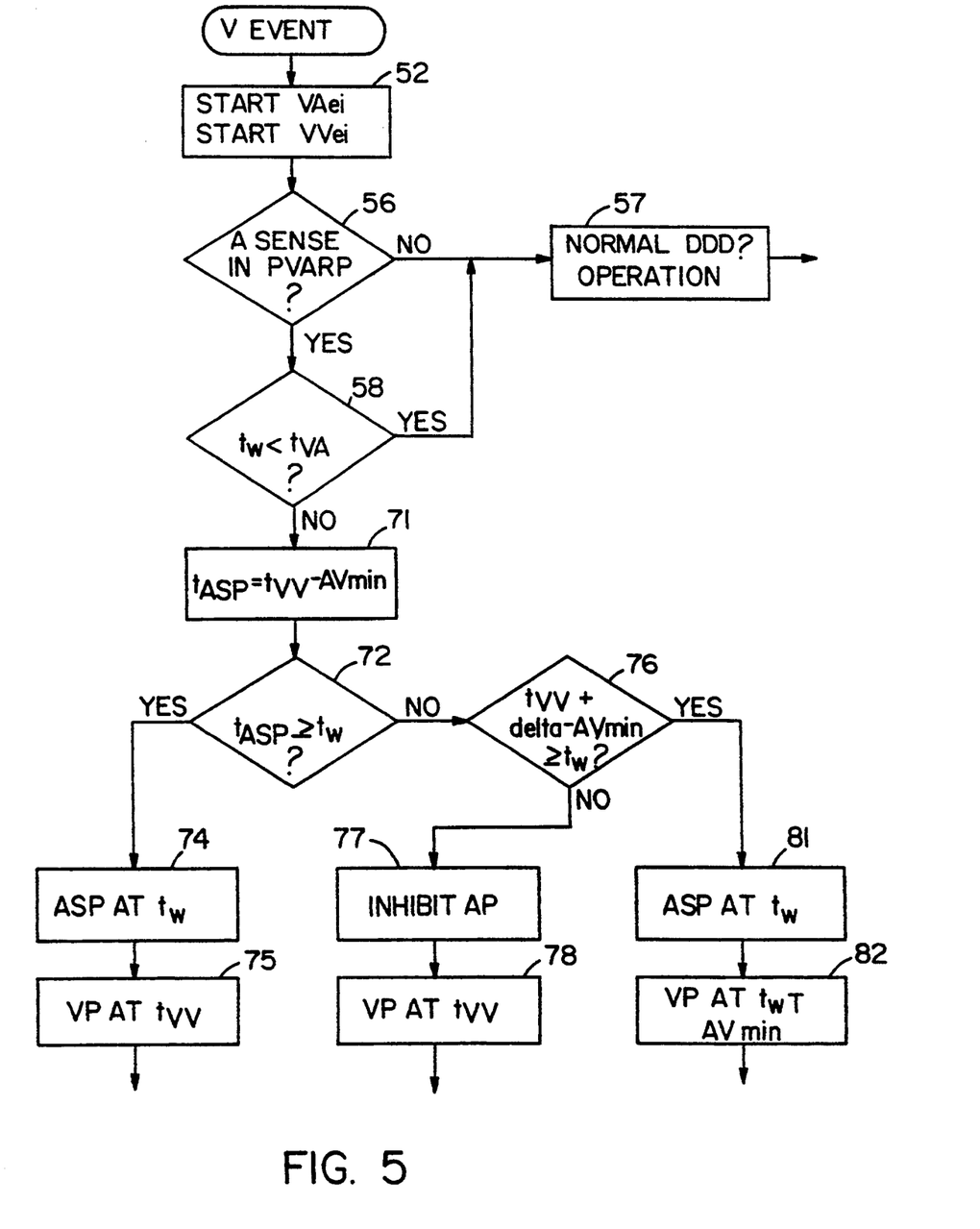
FIG. 5 is a flow chart showing the basic logic steps taken by a hardware and/or software of a preferred embodiment of this system, and illustrating the method of this invention for providing atrial sync pulses in response to early atrial senses.

Referring now to FIG. 5, there is shown a flow diagram of the primary logical functions carried out by a pacemaker embodiment of this invention, in order to attempt to deliver an ASP. Following a V event (sensed or paced) at block 52 the pacemaker initiates time out of $VA_{ei}$ and time out of $VV_{ei}$, both of which can be rate controlled, e.g., a function of activity and/or QT sensing. Suitably, the microprocessor controls a clock which starts at the ventricular event, the clock being compared to stored values for $VA_{ei}$, $VV_{ei}$, and the time corresponding to the upper rate limit for tracking atrial senses. By this manner, when the pacemaker determines an AS, it can determine whether it has occurred during the time designated here as PVARP, which time can vary as a function of rate signals developed in a rate responsive dual chamber pacemaker. At block 56, it is determined whether there has been an A sense in the early atrial sense period, e.g., PVARP. If not, then control branches to block 57, and normal DDD, DDDR, DDI or DDIR pacing is carried out. However, if there has been an A sense detected in PVARP, then the pacemaker logic determines whether $t_w$ is less than $t_{VA}$. If yes, there is no reason for an ASP, and the logic returns to 57. Assuming $t_w \geq t_{VA}$ the delivery of an AP during AIW is inhibited, and $t_{ASP}$ is calculated as $t_{vv}-AV_{min}$, as shown in block 71. At 72, this value of $t_{ASP}$ is compared to $t_w$. If it is greater than $t_w$, this means that an atrial sync pulse can be delivered. The pacemaker goes to block 74, where the pacemaker delivers the ASP at $t_w$, and at 75, the ventricular pulse is delivered at $t_{vv}$.

Returning to block 72, if the calculation shows that $t_{ASP}$ would come before $t_w$, the control branches to block 76. A determination is made at 76 as to whether an ASP can be delivered by extending the V-V interval ($VV_{ei}$) by no more than delta. In other words, is $t_{vv}+$ delta$-AV_{min}$ at or after $t_w$? If the answer is no, the pacemaker branches to block 77, AP is inhibited and VP is delivered at $t_{vv}$. If the answer is yes, the pacemaker branches to block 81 and delivers an ASP at $t_w$ and a VP at $t_w+AV_{min}$ (block 82). Thus, for this latter case, the V-V interval is incremented by no more than a predetermined increment.

Figure 6A:
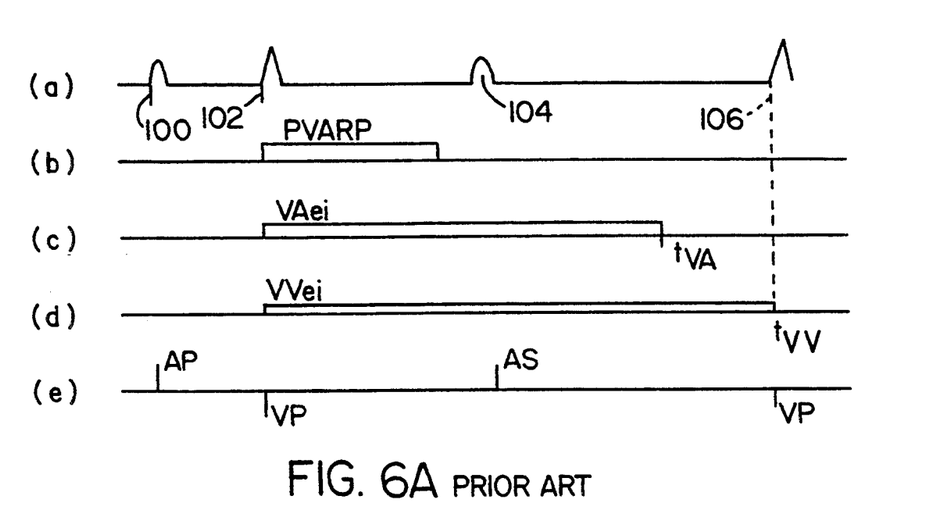
FIGS. 6A and 6B comprise timing diagrams illustrating a beneficial method of employing the atrial sync pulse feature in a DDI or DDIR pacer.
Figure 6B:
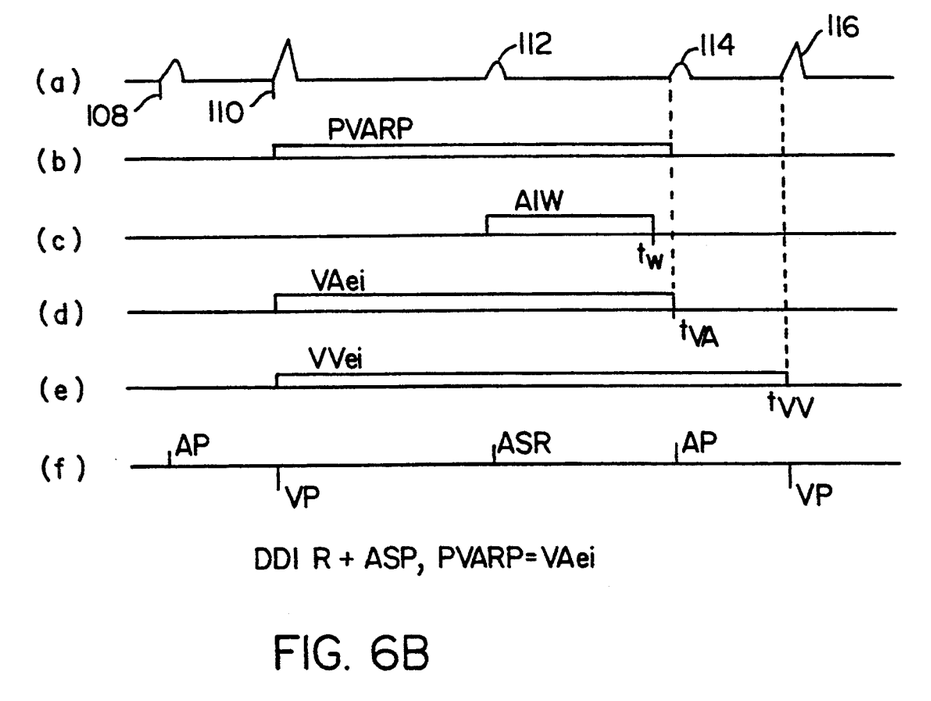

FIGS. 6A and 6B illustrate the manner in which the atrial sync pace feature may be employed to provide an improved DDIR pacing mode. As illustrated in the uppermost of the two timing charts, traditional DDIR pacing employs a PVARP substantially shorter than the V-A interval ($VA_{ei}$). As illustrated in the ECG tracing, in the absence of a sensed atrial depolarization, atrial and ventricular pacing pulses are generated sequentially at 100 and 102. A spontaneous atrial depolarization 104, after the expiration of the PVARP inhibits the generation of an atrial pacing pulse, with a ventricular pacing pulse being generated at 106 at $t_{vv}$. The result is a loss of atrial synchrony, in exchange for the ability to avoid atrial competitive pacing.

By employing the atrial sync pulse invention in conjunction with a pacemaker programmed to DDI or DDIR pacing mode, and by specifying that the PVARP is to be set equal to or slightly less than $VA_{ei}$, competitive atrial pacing can be avoided while maintaining atrial-ventricular synchrony. As illustrated in the lower set of tracings, sequential atrial and ventricular pacing pulses are generated at 108 and 110. At 112, a spontaneous atrial depolarization is illustrated, initiating timing of the atrial inhibition window (AIW). Because the AIW expires before the VA escape interval, an atrial pacing pulse 114 is generated at the expiration of the VA interval, followed thereafter by a ventricular pacing pulse 116 at the expiration of the normal AV interval.

Had the atrial depolarization 112 been sensed such that the AIW expired following the expiration of the V-A interval, the atrial sync pulse feature would determine when and whether an atrial pacing pulse would be delivered, according to the rules discussed above. For example, if the AIW expired less than the minimum AV interval prior to the scheduled ventricular pacing pulse at $t_{vv}$, the atrial sync pulse would be delivered at the expiration of the atrial inhibition window. Similarly, the mechanism for extending $VV_{ei}$ to accommodate an ASP would also be available. The result is an improved DDI or DDIR pacing mode in which atrial synchrony is safely maintained in the presence of atrial rates below the currently effective pacing rates.

The system and method of this invention are seen to provide a response to early atrial depolarizations in a manner that ensures avoidance of competitive pacing, and maintains regularity of ventricular pacing. This invention enables utilization of the rate responsive information available in a DDIR or DDDR pacer, by maintaining the ventricular escape interval as set by the sensor, and also achieves synchronous pacing whenever possible. By continuously looking for any ASR, the pacemaker is primed to sense occurrences of ASRs during the time of greatest risk, namely when the rate responsive pacing rate is relatively high. Although specific software embodiments have been presented, it is to be understood that the atrial sync pacing method of this invention can be carried out with somewhat different sequences, and in combination with other pacemaker functions.

What is claimed:

1. A cardiac pacemaker, comprising:
   an atrial pulse generator;
   a ventricular pulse generator;
   an atrial sense amplifier responsive to atrial depolarizations;
   a ventricular sense amplifier responsive to ventricular depolarizations;
   timing means comprising means for defining atrial escape intervals, means for defining ventricular escape intervals, means for triggering said atrial pulse generator and means for triggering said ventricular pulse generator to deliver atrial and ventricular pacing pulses at the expirations of said atrial and ventricular escape intervals, respectively;
   means for defining an early atrial sense period following a ventricular depolarization sensed by said ventricular sense amplifier and means for determining when an atrial depolarization has been sensed by said atrial amplifier within said early atrial sense period;
   control means comprising means for defining a first interval initiated at the occurrence of an atrial depolarization sensed within said early sense period, means responsive to the time of expiration of a said atrial escape interval occurring within said first interval for preventing triggering of said atrial pulse generator at the expiration of said atrial escape interval;
   means responsive to the time of expiration of said atrial escape interval occurring during said first interval for defining a second interval as a function of the next time of expiration of a said ventricular escape interval; and
   means for triggering delivery of sequential atrial and ventricular pacing pulses by said atrial and ventricular pulse generators following expiration of said first interval if said first interval expires during said second interval and means for triggering delivery of a ventricular pacing pulse by said ventricular pulse generator without prior triggering of said atrial pulse generator if said first interval expires after said second interval.

2. A cardiac pacemaker according to claim 1 wherein said means for defining said second interval comprises means for defining a second interval which ends prior to said next time of expiration of said ventricular escape interval.

3. A cardiac pacemaker according to claim 1 or claim 2 wherein said triggering means comprises means for triggering of said ventricular pulse generator at said next time of expiration of said ventricular escape interval in response to said first time interval expiring after said second time interval.

4. A cardiac pacemaker according to claim 1 wherein said means for defining said second interval comprises means for initially defining said second interval ending at a first time prior to said next time of expiration of said ventricular escape interval and means for redefining said second interval to end at a later time in response to said first interval expiring after said initially defined second interval.

5. A cardiac pacemaker according to claim 4 wherein said triggering means further comprises means for triggering delivery of sequential atrial and ventricular pacing pulses by said atrial and ventricular pulse generators following expiration of said first interval if said first interval expires during said redefined second interval and means for triggering delivery of a ventricular pacing pulse by said ventricular pulse generator without prior triggering of said atrial pulse generator if said first interval expires after said redefined second interval.

6. A cardiac pacemaker according to claim 4 wherein said triggering means further comprises means for triggering delivery of sequential atrial and ventricular pacing pulses by said atrial and ventricular pulse generators, following expiration of said first interval such that said atrial and ventricular pacing pulses are separated by a third predetermined time interval, if said first interval expires after said initially defined second interval and during said redefined second interval and means for triggering delivery of a ventricular pacing pulse by said ventricular pulse generator at said next time of expiration of said ventricular escape interval without prior triggering of said atrial pulse generator if said first interval expires after said redefined second interval.

7. A cardiac pacemaker according to claim 1 wherein said triggering means further comprises means for triggering delivery of an atrial pacing pulse at the expiration of said first interval and delivery of a ventricular pacing pulse at the said next time of expiration of said ventricular escape interval if said first interval expires during said second interval and means for triggering delivery of a ventricular pacing pulse at the said next time of expiration of said ventricular escape interval without prior triggering of said atrial pulse generator if said first interval expires after said second interval.

8. A method of cardiac pacing, comprising:
   sensing atrial and ventricular depolarizations;
   defining atrial and ventricular escape intervals and delivering atrial and ventricular pacing pulses at the expirations of said atrial and ventricular escape intervals, respectively;
   defining an early atrial sense period following a ventricular depolarization sensed by said ventricular sense amplifier determining when an atrial depolarization has been sensed within said early atrial sense period;
   defining a first interval initiated at the occurrence of an atrial depolarization sensed within said early sense period and in response to the time of expiration of a said atrial escape interval occurring within said first interval, preventing delivery of an atrial pacing pulse at the expiration of said atrial escape interval;
   in response to the time of expiration of said atrial escape interval occurring during said first interval, defining a second interval as a function of the next time of expiration of a said ventricular escape interval; and
   delivering sequential atrial and ventricular pacing pulses following expiration of said first interval if said first interval expires during said second interval and delivering a ventricular pacing pulse without prior delivery of an atrial pacing pulse generator if said first interval expires after said second interval.

9. A method according to claim 8 wherein said step of defining said second interval comprises defining a second interval which ends prior to said next time of expiration of said ventricular escape interval.

10. A method according to claim 8 or claim 9 wherein said delivering step comprises delivering of a ventricular pacing pulse at said next time of expiration of said ventricular escape interval in response to said first time interval expiring after said second time interval.

11. A method according to claim 8 wherein said step of defining said second interval comprises initially defining said second interval ending at a first time prior to said next time of expiration of said ventricular escape interval and redefining said second interval to end at a later time in response to said first interval expiring after said initially defined second interval.

12. A method according to claim 11 wherein said delivering step comprises delivering sequential atrial and ventricular pacing pulses following expiration of said first interval if said first interval expires during said redefined second interval and delivering a ventricular pacing pulse without prior delivery of an atrial pacing pulse if said first interval expires after said redefined second interval.

13. A method according to claim 11 wherein said delivering step comprises delivering sequential atrial and ventricular pacing pulses following expiration of said first interval such that said atrial and ventricular pacing pulses are separated by a third time interval, extending past said next time of expiration of said ventricular escape interval if said first interval expires after said initially defined second interval and during said redefined second interval and delivering a ventricular pacing pulse at said next time of expiration of said ventricular escape interval without prior delivery of an atrial pacing pulse if said first interval expires after said redefined second interval.

14. A cardiac pacemaker according to claim 8 wherein said delivering step comprises delivering an atrial pacing pulse at the expiration of said first interval and delivering a ventricular pacing pulse at the said next time of expiration of said ventricular escape interval if said first interval expires during said second interval and delivering a ventricular pacing pulse at the said next time of expiration of said ventricular escape interval without prior delivery of said atrial pulse generator if said first interval expires after said second interval.

* * * * *